(12) United States Patent
Gerharz et al.

(10) Patent No.: US 9,693,560 B2
(45) Date of Patent: Jul. 4, 2017

(54) MICROBICIDE SUBSTANCES

(71) Applicant: LANXESS Deutschland GmbH, Cologne (DE)

(72) Inventors: Tanja Gerharz, Solingen (DE); Peter Wachtler, Krefeld (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 14/911,308

(22) PCT Filed: Aug. 25, 2014

(86) PCT No.: PCT/EP2014/067970
§ 371 (c)(1),
(2) Date: Feb. 10, 2016

(87) PCT Pub. No.: WO2015/028414
PCT Pub. Date: Mar. 5, 2015

(65) Prior Publication Data
US 2016/0198712 A1 Jul. 14, 2016

(30) Foreign Application Priority Data

Aug. 28, 2013 (EP) .................................... 13182078

(51) Int. Cl.
*A01N 43/80* (2006.01)
*A01N 47/44* (2006.01)
*C09C 3/08* (2006.01)

(52) U.S. Cl.
CPC ............. *A01N 47/44* (2013.01); *A01N 43/80* (2013.01); *C09C 3/08* (2013.01)

(58) Field of Classification Search
CPC ........... A01N 43/80; A01N 47/44; C09C 3/08
See application file for complete search history.

(56) References Cited

U.S. PATENT DOCUMENTS

| | | | | |
|---|---|---|---|---|
| 4,661,503 A | * | 4/1987 | Martin | A01N 47/44 210/764 |
| 5,955,486 A | * | 9/1999 | Mattox | A01N 43/80 424/630 |
| 6,361,788 B1 | | 3/2002 | Antoni-Zimmrmann et al. | |
| 6,770,677 B2 | * | 8/2004 | Carlson | A01N 47/02 514/579 |
| 6,890,969 B2 | * | 5/2005 | Rabasco | A01N 33/12 424/405 |
| 9,420,791 B2 | * | 8/2016 | Uhr | A01N 43/80 |

FOREIGN PATENT DOCUMENTS

WO 2011/003906 A2 * 1/2011
WO 2013/026889 A1 * 2/2013

OTHER PUBLICATIONS

SciFinder Scholar Data Sheet on Kathon accessed on Sep. 14, 2016.*
Kull, et al. "Mixtures of Quaternary Ammonium Compounds and Long-chain Fatty Acids as Antifungal Agents", Appl Microbiol. Nov. 1961; 9(6): 538-541, American Society for Microbiology (ASM).
International Search Report from International Application No. PCT/EP2014/067970, dated Oct. 22, 2014, two pages.

* cited by examiner

*Primary Examiner* — Alma Pipic

(57) ABSTRACT

The present application relates to biocidal substances comprising at least one isothiazolinone from the group consisting of 1,2-benzisothiazolin-3-one (BIT) and 2-methyl-4-isothiazolin-3-one (MIT), and at least one N-alkyl-guanidinium salt, methods for the production thereof, and their use for protecting technical materials and products which can be attacked by microorganisms.

12 Claims, No Drawings

MICROBICIDE SUBSTANCES

The present application relates to biocidal substances comprising at least one isothiazolinone from the group consisting of 1,2-benzisothiazolin-3-one (BIT) and 2-methyl-4-isothiazolin-3-one (MIT), and at least one N-alkyl-guanidinium salt, to methods for the production thereof, and to their use for protecting technical materials and products which can be attacked by microorganisms.

N-alkylguanidine salts have good bactericidal effectiveness, good rate of action and are very readily soluble in water. However, the use of relatively large amounts of N-alkyl-guanidinium salts may lead to foaming, which hinders the use or makes it impossible. Furthermore, in practice very high dosage amounts may be necessary in some cases to achieve satisfactory results. Furthermore, the high solubility in water can be disadvantageous for exterior applications since weathering rapidly leads to them being washed out.

From U.S. Pat. No. 4,661,503 synergistic mixtures of dodecylguanidinium hydrochloroide with a mixture of 5-chloro-2-methyl-4-isothiazolin-3-one (CMIT) and MIT in a weight ratio of about 3 to 1, which are said to have a good effect against bacteria and fungi. However, it is desirable to further improve such mixtures.

BIT and its salts, such as in particular its sodium, potassium and lithium salts, are active ingredients that have been used in practice for a long time for producing microbicidally effective formulations. BIT is notable for good chemical and thermal stability and in principle has a broad antimicrobial effect (bacteria, fungi, yeasts). However, the efficacy against certain types of bacteria is not always satisfactory and the observed rate of action is often insufficient for avoiding microbiologically induced material damage.

To improve the efficacy and efficiency of BIT, it is known for example from EP 1 005 271 A1 to add MIT and optionally further biocides such as, for example, formaldehyde or formaldehyde-releasing substances.

However, an improvement in the activity spectrum, the rate of action or the amount of biocides to be used overall is also desirable for such mixtures.

Biocidal substances have been found which comprise
(a) at least one isothiazolinone from the group consisting of 1,2-benzisothiazolin-3-one and 2-methyl-4-isothiazolin-3-one
and
(b) at least one N-alkyl-guanidinium salt,
where, if the biocidal substances comprises only 2-methyl-4-isothiazolin-3-one as component (a), the biocidal substance furthermore comprises either no 5-chloro-2-methyl-4-isothiazolin-3-one or
comprises 5-chloro-2-methyl-4-isothiazolin-3-one, where then the weight ratio of 2-methyl-4-isothiazolin-3-one to 5-chloro-2-methyl-4-isothiazolin-3-one is at least 0.35:1, preferably at least 1:1, such as, for example, 1:1 to 1000:1, particularly preferably at least 2:1, such as, for example, 2:1 to 1000:1, very particularly preferably at least 10:1, such as, for example, 10:1 to 1000:1 and yet further preferably at least 50:1, such as, for example, 50:1 to 1000:1.

Besides the specified ranges and preferred ranges of formulae and parameters, the scope of the invention also includes any desired combinations thereof, even if they are not explicitly listed in their entirety below for practical reasons.

The mixtures according to the invention have a strong effect against microorganisms such as bacteria, fungi, yeast and algae and can be used for protecting technical materials against attack and destruction by microorganisms.

According to the invention, N-alkyl-guanidinium salts are understood as meaning compounds which have at least one guanidinium group or biguanide group, which have an alkyl radical on at least one of their nitrogen atoms, or compounds in which, in each case two groups selected from guanidinium groups and biguanide groups, are linked via at least in each case one of their nitrogen atoms via an alkylene radical. Examples of compounds of the latter type include chlorohexidine and polyhexanide.

Preferred N-alkyl-guanidinium salts are those of formula (I)

$$[H_2N-(C=NH_2)-NH-R]^+X^- \quad (I)$$

in which R is a $C_8$-$C_{18}$ alkyl radical and $X^-$ is a monovalent anion or 1/p equivalents of a p-valent anion, where p is a natural number of 2 or more.

R is preferably n-dodecyl, $X^-$ is preferably formate, acetate, nitrate, halide such as, for example, chloride or bromide.

Particularly preferred compounds of formula (I) are n-dodecylguanidinium acetate and n-dodecylguanidinium chloride.

Preferred biocidal substances comprise, as component (a), 1,2-benzisothiazolin-3-one and 2-methyl-4-isothiazolin-3-one.

The relative ratios of components (a) and (b) can be varied in the mixtures according to the invention over a wide range.

For example, the weight ratio of components (a) and (b) to one another is for example 10:1 to 1:10, preferably 5:1 to 1:5 and particularly preferably 2:1 to 1:5.

If BIT and MIT are used as component (a), their weight ratio is for example 1:100 to 100:1 preferably 3:1 to 1:3 and particularly preferably 1.5:1 to 1:2.5.

The substances according to the invention are exceptionally suitable as preservatives for technical materials. The term "technical materials" includes in general, but without limitation thereto, the following materials and products:
  paints, inks, plasters and other coating compositions
  starch solutions and slurries or other products produced on the basis of starch, such as e.g. printing thickeners
  slurries of other raw materials such as color pigments (e.g. iron oxide pigments, carbon black pigments, titanium dioxide pigments) or slurries of inorganic fillers and pigments such as kaolin, calcium carbonate, gypsum, bentonite, magnesium silicate, smectite or talc,
  construction chemical products such as concrete additives, for example based on molasses, lignosulfonate or polyacrylates, bitumen emulsions or joint sealants
  glues or adhesives based on known animal, vegetable or synthetic raw materials
  polymer dispersions based on e.g. polyacrylate, polystyrene acrylate, styrene butadiene, polyvinyl acetate, etc.
  detergents and cleaners for industrial and household use
  mineral oils and mineral oil products (such as e.g. diesel fuels)
  cooling lubricants for metal working based on mineral oil-containing, semisynthetic or synthetic concentrates
  auxiliaries for the leather, textile or photochemical industry
  preproducts and intermediates of the chemical industry, e.g. during dye production and storage
  inks or washes
  wax and clay emulsions.

Preferably, the technical materials are:
starch solutions and slurries or other products produced on the basis of starch such as e.g. printing thickeners
slurries of other raw materials such as colored pigments (e.g. iron oxide pigments, carbon black pigments, titanium dioxide pigments) or slurries or inorganic fillers and pigments such as kaolin, calcium carbonate, gypsum, bentonite, magnesium silicate, smectite or talc.

Particularly preferably, the technical materials are:
slurries of inorganic fillers and pigments such as kaolin, calcium carbonate, gypsum, bentonite, magnesium silicate, smectite or talc, with slurries of calcium carbonate being yet further preferred.

The substances according to the invention can be used particularly efficiently in a method for protecting technical materials against infestation with and/or destruction by microorganisms. They are especially effective against bacteria, fungi and slime organisms. By way of example, mention may be made of the following microorganisms:

Bacteria:
*Alcaligenes* such as *Alcaligenes faecalis*, *Bacillus* such as *Bacillus subtilis*, *Citrobacter* such as *Citrobacter freundii*, *Corynebacterium* such as *Corynebacterium ammoniagenes*, *Enterobacter* such as *Enterobacter aerogenes*, *Enterococcus* such as *Enterococcus hirae*, *Escherichia* such as *Escherichia coli*, *Proteus* such as *Proteus hauseri*, *Pseudomonas* such as *Pseudomonas aeruginosa*, *Pseudomonas fluorescens* or *Pseudomonas stutzeri*, *Salmonella* such as *Salmonella enterica*, *Staphylococcus* such as *Staphylococcus aureus*;

Fungi:
*Acremonium* such as *Acremonium stricturn*, *Alternaria* such as *Alternaria tenuis* or *Alternaria alternata*, *Aspergillus* such as *Aspergillus niger* or *Aspergillus brasiliensis*, *Candida* such as *Candida albicans*, *Chaetomium* such as *Chaetoinium globosum*, *Fusarium* such as *Fusarium solani*, *Geotrichum* such as *Geotrichum candiduria*, *Lentinus* such as *Lentinus tigrinus*, *Penicillium* such as *Penicillium glaucum* or *Penicillium pinophilum*, *Rhodotorula* such as *Rhodotorula rubra* or *Rhodotorula mucilaginosa*, *Stachybotrys* such as *Stachybotrys chartanim*, *Trichoderma* such as *Trichoderma virens*.

The mixtures according to the invention can comprise, as component c), additionally either no, one or more further biocidal active ingredients. For example, these further biocidal active ingredients can be selected from the group consisting of bronopol, benzylhemiformal, trimethylene-2-methylisothiazolinon-3-one, N-methyylbenzisothiazolinone, 2-n-ortylisothiazolin-3-one, tetramethylolacetylene-diurea (TMAD), 1,3-bis(hydroxymethyl)-5,5-dimethylimidazolidine-2,4-dione (DMDMH), p-chloro-m-cresol, dimethyiolurea, 1,2-dibromo-2,4-dicyanobutane, 2,2-dibromo-3-nitrilopropioriamide, glutardialdehyde, ethylene glycol hemiformal, ethylene glycol bis-hemiformal, N-methylolurea, thiabendazole, carbendazim, zinc pyrithione, sodium pyrithione, 2-phenoxyethanol, phenoxypropariol, o-phenylphenol, chlorophene and quaternary ammonium salts, such as e.g. N-alkyl-N,N-dimethyibenzylammonium chloroide, and CMIT with the limitations mentioned at the start.

The application concentrations of the substances according to invention and the ratio of components (a) and (b) and the optionally present further active ingredients is governed by the type and occurrence of the microorganisms to be controlled, the microbial starting load, and also by the composition of the material to be protected. The optimum use amount for a specific application can be easily ascertained prior to use in practice by test series in the laboratory in a manner sufficiently known to the person skilled in the art.

Furthermore, the invention also encompasses the technical materials treated with the substances according to the invention.

In general, in total 2 to 50 000 ppm of components (a) and (b), preferably 5 to 5000 ppm, particularly preferably 10 to 2000 ppm and particularly preferably 200 to 1000 ppm, are present in the technical material for preservation. The invention therefore also encompasses technical materials which have been treated with substances according to the invention, or in another embodiment comprise the aforementioned amounts of components (a) and (b).

In the substances according to the invention, the sum of components (a) and (b) can be varied within a broad range. In general, the sum of components (a) and (b) is 1 to 80% by weight, preferably 2 to 70% by weight and particularly preferably 4 to 50% by weight, based on the total weight of the substances according to the invention.

The fraction of further active ingredients optionally used in the substances according to the invention as component (c) can vary within a wide range and depends heavily on the nature of the active ingredient and medium to be protected. In general, it can be between 0.2 and 20% by weight, preferably between 0.5 and 10% by weight and particularly preferably between 0.5 and 5% by weight, based on the total weight of the concentrates or formulations.

In further aspects, the invention encompasses the use, independent in each case, of MIT or BIT or N-alkyl-guanidinium salts for producing the substances according to the invention or technical materials.

The substances according to the invention can, depending on their particular physical and/or chemical properties, either be used separately in the form of a metered addition of the individual active ingredient to the technical material to be protected, in which case an individual adjustment of the concentration ratio can be performed depending on the requirements of the preservation problem to be solved, or the metered addition of a finished biocidal substance comprising components (a) and (b) can take place.

The formulation of the substances according to the invention is arbitrary and can take place for example in the form of solutions, emulsions, suspensions, powders, foams, pastes, granules, aerosols and microencapsulations in polymeric substances.

The substances according to the invention may therefore in each case further comprise or not comprise:
Interface-active substances, such as, for example, surfactants. Surfactants can be, for example, nonionic, cationic and amphoteric surfactants, preferably anionic surfactants. Suitable anionic surfactants are, for example, alkyl sulfates, alkyl ether sulfates, alkylaryl sulfonates, alkyl succinates, alkyl sulfosuccinates, N-alkoylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and also ammonium and triethanolamine salts. The alkyl ether sulfates, alkyl ether phosphates and alkyl ether carboxylates can in each case have for example between 1 and 10 ethylene oxide or propylene oxide units, preferably 1 to 3 ethylene oxide units. Of suitability are, for example, sodium lauryl sulfate, ammonium lauryl sulfate, sodium lauryl ether sulfate, ammonium lauryl ether sulfate, sodium lauryl sarcosinate, sodium oleyl succinate, ammonium lauryl salfosuccinate, sodium dodecylhenzenesulfonate, triethanolamine dodecylbenzenesulfonate.

Wetting agents, such as, for example, alkali metal salts, alkaline earth metal salts, ammonium salts of aromatic sulfonic acids, e.g. ligno-, phenol-, naphthalene- and dibutylnaphthalenesulfonic acid, and also of fatty acids, alkyl- and alkylarylsulfonates, alkyl, lauryl ether and fatty alcohol sulfates, and also salts of sulfated hexa-, hepta- and octaderanols or fatty alcohol glycol ethers, condensation products of sulfonated naphthalene and its derivatives with formaldehyde, condensation products of naphthalene or of naphthalenesulfonic acids with phenol and formaldehyde, polyoxyethylene octyl phenol ether, ethoxylated isooctyl-, octyl- or nonylphenol, alkylphenol or tributylphenyl polyglycol ether, alkylayl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbital esters, ligno sulfite waste liquors or methylcellulose.

Emulsifiers, such as, for example, sodium, potassium and ammonium salts of straight-chain aliphatic carboxylic acids of chain length $C_{12}$-$C_{20}$, sodium hydroxyoctadecanesulfonate, sodium, potassium and ammonium salts of hydroxy fatty acids of chain length $C_{12}$-$C_{20}$ and sulfation or acetylation products thereof, alkyl sulfates, also as triethanolamine salts, alkyl-($C_{10}$-$C_{20}$)-sulfonates, alkyl($C_{10}$-$C_{20}$)-arylsulfonates, dimethyldialkyl ($C_8$-$C_{18}$)-ammonium chloride, acyl, alkyl, oleyl and alkylaryl oxethylates and their sulfation products, alkali metal salts of the sulfosuccinic acid esters with aliphatic saturated monohydric alcohols of chain length $C_4$-$C_{16}$, sulfosuccinic acid 4-esters with polyethylene glycol ethers of monohydric aliphatic alcohols of chain length $C_{10}$-$C_{12}$ (disodium salt), sulfosuccinic acid 4-esters with polyethylene glycol nonylphenyl ether (disodium salt), sulfosuccinic acid bis-cyclohexylester (sodium salt), lignosulfonic acid, and calcium, magnesium, sodium and ammonium salts thereof, polyoxyethylene sorbitan monooleate with 20 ethylene oxide groups, resin acids, hydrogenated and dehydrogenated resin acids, and alkali metal salts thereof, dodecylated diphenyl ether disulfonic acid sodium, and copolymers of ethylene oxide and propylene oxide with a minimum content of 10% by weight of ethylene oxide. Preferably, the emulsifiers used are: sodium lauryl sulfate, sodium lauryl ether sulfate, ethoxylated (3 ethylene oxide groups); the polyethylene glycol (4-20) ethers of oleyl alcohol, and the polyethene oxide-(4-14) ethers of nonylphenol.

Dispersants, such as, for example, alkylphenol polyglycol ethers.

Stabilizers, such as, e.g. cellulose and cellulose derivatives.

Adhesives and thickeners, such as carboxymethylcellulose, natural and synthetic pulverulent, granular or latex-like polymers are used, such as gum arabic, polyvinyl alcohol, polyvinyl acetate, and natural phospholipids, such as cephalins and lecithins and synthetic phospholipid, and mineral or vegetable oils.

Spreading agents, such as, for example, isopropyl myristate, polyoxyethylene nonyl phenyl ether and polyoxyethylene lauryl phenyl ether.

Organic solvents, such as, for example, mono- or polyhydric alcohols, esters, ketones and hydrocarbons. Examples of suitable solvents are paraffins, e.g. petroleum fractions, mineral and vegetable oils, butanol or glycol, and ethers and esters thereof, ketones such as acetone, methyl ethyl ketone, methyl isobutyl ketone or cyclohexanone.

Fragrances and dyes, such as inorganic pigments, e.g. iron oxide, titanium oxide, Prussian blue and organic dyes, such as alizarin, azo and metallophthalocyanine dyes and trace nutrients such as salts of iron, manganese, boron, copper, cobalt, molybdenum and zinc.

Dedusting agents, such as, for example, polyglycols and polyglycol ethers. The at least essentially solid formulations here can comprise, for example, in each case 0.01 to 2, preferably 0.05 to 1, particularly preferably 0.1 to 0.5% by weight, of dedusting agents.

Buffer substances, buffer systems or pH regulators. The at least essentially solid formulations can here comprise for example in each case 0.01 to 10, preferably 0.1 to 5, % by weight of buffer substances, buffer systems or pH regulators.

Solid carriers such as, for example, natural stone flours, such as kaolins, clay earths, talc, chalk, quartz, attapulgite, montmorillonite or diatomerous earths, as well as synthetic stone flours, such as highly dispersed silica, aluminum oxide and silicates;

Examples of suitable solid carriers especially for granules are: broken and fractionated natural stones such as calcite, marble, pumice, sepiolite, dolomite, and synthetic granules made of inorganic and organic flours, and also granules made of organic materials such as saw dust, coconut shells, corn cobs and tobacco stems; water The particular advantage of the invention lies in the provision of unusually highly effective predominantly synergistic biocidal substances with a broad activity spectrum and high rate of action which are significantly increased compared to combinations of BIT and MIT alone.

EXAMPLES

The growth of bacteria and fungi upon the addition of different biocidal mixtures was tested. The concentration above which growth is no longer detected is given as the minimum inhibitory concentration (MIC). The precultivation of the bacteria which were used in the test was performed on tryptone soya agar. The precultivation of the fungi which were used in the test was performed on malt extract agar. The growth in the MIC tests was checked in tryptone soya broth (bacteria) or malt extract Bouillon (fungi). The organisms were incubated at 26° C. and a relative broth humidity of 70 to 80%. The bacteria were evaluated after 4 days, and the fungi were evaluated atmospheric after 7 days.

The synergistic index (SI) was determined in accordance with the method described by Kull et al. (F. C. Kull et al., Applied Microbiology 9 (1961), 538-541).

The following equation applies here: SI=QA/Qa+QB/Qb $$Qa \times \frac{MIC(A+B)}{MIC(A)} \oplus Qb \times \frac{MIC(A+B)}{MIC(B)} = SI$$

$Q_a$=fraction of substance A
$Q_b$=fraction of substance B

MIC(A)=concentration of substance A which suppresses germ growth

MIC(B)=concentration of substance B which suppresses germ growth

MIC(A+B)=concentration of A+B which suppresses germ growth

If SI has a value above 1, this means that an antagonism is present.

If SI assumes the value 1, this means that an addition of the effect is present.

If SI assumes of below 1, this means that a synergism exists.

Example 1

The effect of an active ingredient combination of BIT and MIT in the weight ratio of 1:1 and varying amounts of dodecylguanidine hydrochloride (DGH, data likewise refer to weight ratios) was tested.

Table 1: gives the MIC values for various bacteria
Table 2: gives the synergy indices calculated for the results according to table 1
Table 3: gives the MIC values for various fungi
Table 4: gives the synergy indices calculated for the results according to table 3

TABLE 1

| Strain | BIT:MIT (1:1) | 1:1 | 2:3 | 1:4 | 1:9 | DGH |
|---|---|---|---|---|---|---|
| Bacillus subtilis | 10 | 5 | 5 | 2.5 | 5 | 5 |
| Citrobacter freundii | 25 | 10 | 10 | 5 | 10 | 10 |
| Corynebacterium ammoniagenes | 62.5 | 5 | 5 | 2.5 | 5 | 5 |
| Enterococcus hirae | 25 | 5 | 5 | 1.75 | 5 | 5 |
| Pseudomonas aeruginosa | 25 | 25 | 25 | 25 | 25 | 50 |
| Staphylococcus aureus | 25 | 2.5 | 1 | 1 | 2.5 | 2.5 |

TABLE 2

| Strain | 1:1 | 2:3 | 1:4 | 1:9 |
|---|---|---|---|---|
| Bacillus subtilis | 0.75 | 0.80 | 0.45 | 0.95 |
| Citrobacter freundii | 0.70 | 0.76 | 0.44 | 0.94 |
| Corynebacterium ammoniagenes | 0.54 | 0.63 | 0.41 | 0.91 |
| Enterococcus hirae | 0.60 | 0.68 | 0.29 | 0.92 |
| Pseudomonas aeruginosa | 0.75 | 0.70 | 0.60 | 0.55 |
| Staphylococcus aureus | 0.55 | 0.26 | 0.33 | 0.91 |

TABLE 3

| Strain | BIT:MIT (1:1) | 9:1 | 4:1 | 1.1 | 2:3 | 1:4 | 1:9 | DGH |
|---|---|---|---|---|---|---|---|---|
| Acremonium strictum | 25 | 10 | 7.5 | 2.5 | 1 | 1 | 2.5 | 5 |
| Alternaria alternata | 25 | 10 | 7.5 | 7.5 | 2.5 | 2.5 | 5 | 5 |
| Candida albicans | 50 | 25 | 25 | 25 | 25 | 10 | 25 | 25 |
| Fusarium solani | 62.5 | 37.5 | 37.5 | 37.5 | 37.5 | 37.5 | 37.5 | 50 |
| Geotrichum candidum | 50 | 37.5 | 25 | 25 | 25 | 10 | 25 | 25 |
| Penicillium pinophilum | 175 | 50 | 50 | 17.5 | 10 | 10 | 17.5 | 17.5 |
| Rhodotorula mucilaginosa | 50 | 25 | 25 | 25 | 25 | 10 | 25 | 25 |
| Stachybotrys chartarum | 50 | 50 | 25 | 25 | 25 | 10 | 25 | 25 |
| Trichoderma virens | 175 | 25 | 37.5 | 25 | 25 | 25 | 10 | 37.5 |

TABLE 4

| Strain | 9:1 | 4:1 | 1:1 | 2:3 | 1:4 | 1:9 |
|---|---|---|---|---|---|---|
| Acremonium strictum | 0.56 | 0.54 | 0.30 | 0.14 | 0.17 | 0.46 |
| Alternaria alternata | 0.56 | 0.54 | 0.90 | 0.34 | 0.42 | 0.92 |
| Candida albicans | 0.55 | 0.60 | 0.75 | 0.80 | 0.36 | 0.95 |
| Fusarium solani | 0.62 | 0.63 | 0.68 | 0.46 | 0.72 | 0.74 |
| Geotrichum candidum | 0.83 | 0.60 | 0.75 | 0.80 | 0.36 | 0.95 |
| Penicillium pinophilum | 0.54 | 0.80 | 0.55 | 0.37 | 0.47 | 0.91 |
| Rhodotorula mucilaginosa | 0.55 | 0.60 | 0.75 | 0.80 | 0.36 | 0.95 |
| Stachybotrys chartarum | 1.10 | 0.60 | 0.75 | 0.80 | 0.36 | 0.95 |
| Trichoderma virens | 0.20 | 0.37 | 0.40 | 0.46 | 0.56 | 0.92 |

Example 2

The effect of an active ingredient combination of BIT and MIT in the weight ratio of 1:2 and varying amounts of dodecylguanidine hydrochloride (DGH, data likewise refer to weight ratios) was tested.

Table 5: gives the MIC values for various bacteria
Table 6: gives the synergy indices calculated for the results according to table 5
Table 7: gives the MIC values and synergy indices for various bacteria
Table 8: gives the MIC values for various fungi
Table 9: gives the synergy indices calculated for the results according to table 8
Table 10: gives the MIC values and synergy indices for various fungi

TABLE 5

| Strain | BIT:MIT (1:2) | 3:2 | 1:1 | 1:4 | 1:9 | DGH |
|---|---|---|---|---|---|---|
| Corynebacterium ammoniagenes | 25 | 5 | 5 | 5 | 2.5 | 5 |
| Enterobacter aerogenes | 37.5 | 10 | 10 | 10 | 10 | 10 |
| Enterococcus hirae | 25 | 5 | 5 | 5 | 3.75 | 5 |
| Proteus hauseri | 10 | 5 | 5 | 10 | 10 | 10 |

TABLE 6

| Strain | 3:2 | 1:1 | 1:4 | 1:9 |
|---|---|---|---|---|
| Corynebacterium ammoniagenes | 0.52 | 0.60 | 0.84 | 0.46 |
| Enterobacter aerogenes | 0.56 | 0.63 | 0.85 | 0.93 |
| Enterococcus hirae | 0.52 | 0.60 | 0.84 | 0.69 |
| Proteus hauseri | 0.50 | 0.50 | 1.00 | 1.00 |

TABLE 7

| Strain | BIT/MIT (1:2) | (BIT/MIT (1:2)):DGH (4:1) | DGH | SI |
|---|---|---|---|---|
| Alcaligenes faecalis | 5 | 5 | 10 | 0.90 |
| Bacillus subtilis | 10 | 5 | 2.5 | 0.80 |
| Citrobacter freundii | 17.5 | 10 | 5 | 0.86 |
| Staphylococcus aureus | 25 | 2.5 | 1 | 0.58 |

MIC [ppm]

TABLE 8

| Strain | BIT:MIT (1:2) | 9:1 | 4:1 | 3:2 | 1:1 | 2:3 | 1:4 | DGH |
|---|---|---|---|---|---|---|---|---|
| Acremonium strictum | 25 | 10 | 5 | 2.5 | 2.5 | 2.5 | 2.5 | 2.5 |
| Alternaria alternata | 37.5 | 10 | 5 | 5 | 5 | 5 | 5 | 5 |
| Aspergillus brasiliensis | 250 | 75 | 75 | 82.5 | 25 | 50 | 37.5 | 37.5 |
| Aureobasidium pullulans | 25 | 17.5 | 10 | 5 | 5 | 5 | 5 | 5 |
| Candida albicans | 50 | 25 | 25 | 25 | 25 | 25 | 25 | 25 |
| Chaetomium globosum | 250 | 75 | 50 | 50 | 50 | * | 25 | 25 |
| Fusarium solani | 50 | 25 | 25 | 17.5 | 10 | 25 | 25 | 25 |
| Rhodotorula mucilaginosa | 50 | 25 | 25 | 10 | 10 | 10 | 25 | 25 |
| Trichoderma virens | 250 | 50 | 50 | 50 | 25 | 25 | 25 | 25 |

* not determined

TABLE 9

| Strain | 9:1 | 4:1 | 3:2 | 1:1 | 2:3 | 1:4 |
|---|---|---|---|---|---|---|
| Acremonium strictum | 0.76 | 0.56 | 0.46 | 0.55 | 0.64 | 0.82 |
| Alternaria alternata | 0.44 | 0.31 | 0.48 | 0.57 | 0.65 | 0.83 |
| Aspergillus brasiliensis | 0.47 | 0.64 | 1.08 | 0.38 | 0.88 | 0.83 |
| Aureobasidium pullulans | 0.98 | 0.72 | 0.52 | 0.60 | 0.68 | 0.84 |
| Candida albicans | 0.55 | 0.60 | 0.70 | 0.75 | 0.80 | 0.90 |
| Chaetomium globosum | 0.57 | 0.56 | 0.92 | 1.10 | * | 0.82 |
| Fusarium solani | 0.55 | 0.60 | 0.49 | 0.30 | 0.80 | 0.90 |
| Rhodotorula mucilaginosa | 0.55 | 0.60 | 0.28 | 0.30 | 0.32 | 0.90 |
| Trichoderma virens | 0.38 | 0.56 | 0.92 | 0.55 | 0.64 | 0.82 |

* not determined

TABLE 10

| Strain | BIT/MIT (1:2) | DHG | (BIT/MIT (1:2)):DGH (1:1) | SI |
|---|---|---|---|---|
| Stachybotrys chartarum | 50 | 7.5 | 10 | 0.77 |
| Paecilomyces formosus | 10 | 5 | 7.5 | 0.79 |
| Geotrichum candidum | 50 | 10 | 10 | 0.60 |
| Penicillium pinophilum | 75 | 7.5 | 10 | 0.73 |

MIC [ppm]

The above tables 1-10 clearly show that for three-component mixtures according to the invention of BIT, MIT and DGH in various mixing ratios, a marked synergism against various bacteria and fungi is present.

Example 3

The effect of an active ingredient combination BIT and dodecylguanidine hydrochloride (DGH, data likewise refer to weight ratios) in various weight ratios was tested.

Table 11: shows the MIC values and synergy indices for various fungi at a BIT to DGH weight ratio of 3:2

Table 11 shows the MIC values and synergy indices for various bacteria

Table 13: shows the synergy indices calculated for the results according to table 12

Table 14: shows the MIC values as synergy indices for *Staphylococcus aureus* at various BIT to DGH weight ratios Table 15: shows the MIC values and synergy indices for various fungi Table 16: shows the synergy indices calculated for the results according to table 15

Table 17: shows the MIC values and synergy indices for *Candida albicans* at various BIT to DGH weight ratios

TABLE 11

| Strain | BIT | BIT:DGH (3:2) | DGH | SI |
|---|---|---|---|---|
| Alcaligenes faecalis | 2.5 | 2.5 | 10 | 0.70 |
| Bacillus subtilis | 5 | 2.5 | 3.75 | 0.56 |
| Citrobacter freundii | 10 | 5 | 5 | 0.70 |
| Corynebacterium ammoniagenes | 37.5 | 2.5 | 2.5 | 0.44 |
| Enterobacter aerogenes | 25 | 10 | 10 | 0.64 |
| Enterococcus hirae | 10 | 2.5 | 2.5 | 0.55 |
| Proteus hauseri | 7.5 | 5 | 10 | 0.60 |
| Pseudomonas aeruginosa | 50 | 25 | 25 | 0.70 |
| Pseudomonas stutzeri | 10 | 5 | 5 | 0.70 |
| Salmonella enterica | 10 | 5 | 10 | 0.50 |

MIC [ppm]

TABLE 12

| Strain | BIT | 1:1 | 1:4 | 1:9 | DGH |
|---|---|---|---|---|---|
| Bacillus subtilis | 5 | 3.75 | 2.5 | 2.5 | 3.75 |
| Enterobacter aerogenes | 25 | 10 | 10 | 10 | 10 |
| Proteus hauseri | 7.5 | 7.5 | 5 | 7.5 | 10 |
| Pseudomonas aeruginosa | 50 | 25 | 25 | 25 | 25 |

TABLE 13

| Strain | 1:1 | 1:4 | 1:9 |
|---|---|---|---|
| Bacillus subtilis | 0.88 | 0.63 | 0.64 |
| Enterobacter aerogenes | 0.70 | 0.88 | 0.94 |
| Proteus hauseri | 0.88 | 0.53 | 0.78 |
| Pseudomonas aeruginosa | 0.75 | 0.90 | 0.95 |

TABLE 14

| Active ingredient | Mixing ratio | MIC [ppm] | SI |
|---|---|---|---|
| BIT | | 5 | |
| BIT:DGH | 3:2 | 1 | 0.52 |
| BIT:DGH | 1:1 | 1 | 0.60 |
| BIT:DGH | 2:3 | 0.1 | 0.07 |
| DGH | | 1 | |

TABLE 15

|  | BIT | 9:1 | 4:1 | 3:2 | 1:1 | 2:3 | 1:4 | 1:9 | DGH |
|---|---|---|---|---|---|---|---|---|---|
| *Acremonium strictum* | 17.5 | 7.5 | 10 | 1.75 | 3.75 | 5 | 5 | 5 | 7.5 |
| *Aureobasidium pullulans* | 25 | 10 | 10 | 5 | 5 | 5 | 7.5 | 7.5 | 10 |
| *Chaetomium globosum* | 100 | 75 | 37.5 | 17.5 | 37.5 | 37.5 | 25 | 25 | 37.5 |
| *Fusarium solani* | 37.5 | 37.5 | 10 | 5 | 10 | 10 | 17.5 | 10 | 25 |
| *Geotrichum candidum* | 25 | 10 | 10 | 5 | 10 | 10 | 10 | 10 | 10 |
| *Penicillium pinophilum* | 37.5 | 17.5 | 10 | 5 | 5 | 7.5 | 5 | 5 | 5 |
| *Rhodotorula mucilaginosa* | 25 | 23 | 10 | 5 | 10 | 10 | 10 | 10 | 25 |
| *Trichoderma virens* | 87.5 | 37.5 | 25 | 17.5 | 25 | 25 | 37.5 | 25 | 37.5 |

TABLE 16

|  | 9:1 | 4:1 | 3:2 | 1:1 | 2:3 | 1:4 | 1:9 |
|---|---|---|---|---|---|---|---|
| *Acremonium strictum* | 0.49 | 0.72 | 0.16 | 0.36 | 0.51 | 0.59 | 0.63 |
| *Aureobasidium pullulans* | 0.46 | 0.52 | 0.32 | 0.35 | 0.38 | 0.66 | 0.71 |
| *Chaetomium globosum* | 0.88 | 0.30 | 0.29 | 0.69 | 0.75 | 0.58 | 0.63 |
| *Fusarium solani* | 1.05 | 0.29 | 0.16 | 0.33 | 0.35 | 0.65 | 0.39 |
| *Geotrichum candidum* | 0.46 | 0.52 | 0.32 | 0.70 | 0.76 | 0.88 | 0.94 |
| *Penicillium pinophilum* | 0.77 | 0.61 | 0.48 | 0.57 | 0.98 | 0.83 | 0.91 |
| *Rhodotorula mucilaginosa* | 1.00 | 0.40 | 0.20 | 0.40 | 0.40 | 0.40 | 0.40 |
| *Trichoderma virens* | 0.49 | 0.36 | 0.31 | 0.48 | 0.51 | 0.89 | 0.63 |

TABLE 17

|  | BIT | 9:1 | 4:1 | 3:2 | 1:1 | 2:3 | DGH |
|---|---|---|---|---|---|---|---|
| MIC [ppm] | 25 | 10 | 10 | 5 | 10 | 10 | 25 |
| SI |  | 0.40 | 0.40 | 0.20 | 0.40 | 0.40 |  |

The above tables 11-17 clearly show that for two-component mixtures according to the invention of BIT and DGH in various mixing ratios, a marked synergism against various bacteria and fungi is present.

Example 4

The effect of an active ingredient combination of MIT and dodecylguanidine hydrochloride (DGH, data likewise refer to weight ratios) in various weight ratios was tested.

Table 18: shows the MIC values and synergy indices for various bacteria at a MIT to DGH weight ratio of 9:1
Table 19: shows the MIC values and synergy indices for *Escherichia coli*
Table 20: shows the MIC values and synergy indices for various fungi
Table 21: shows the synergy indices calculated for the results according to table 20
Table 22: shows the MIC values and synergy indices for *Alternaria alternata* at various MIT to DGH weight ratios
Table 23: shows the MIC values and synergy indices for *Stachybotrys chartarum* at various MIT to DGH weight ratios

TABLE 18

| Strain | MIT | 9:1 | DGH | SI |
|---|---|---|---|---|
| *Bacillus subtilis* | 25 | 10 | 2.5 | 0.76 |
| *Salmonella enterica* | 17.5 | 10 | 10 | 0.61 |
| *Staphylococcus aureus* | 50 | 5 | 1 | 0.59 |

TABLE 19

|  | MIT | 3:2 | 1:4 | 1:9 | DGH |
|---|---|---|---|---|---|
| MIC [ppm] | 25 | 7.5 | 5 | 2.5 | 5 |
| SI |  | 0.78 | 0.84 | 0.46 |  |

TABLE 20

| Strain | MIT | 9:1 | 4:1 | 3:2 | 1:4 | DGH |
|---|---|---|---|---|---|---|
| *Aspergillus brasiliensis* | 1000 | 175 | 62.5 | 50 | * | 25 |
| *Candida albicans* | 250 | 50 | 50 | 25 | 25 | 25 |
| *Chaetomium globosum* | 500 | 62.5 | 50 | 50 | 25 | 25 |
| *Fusarium solani* | 250 | 50 | 50 | 25 | 25 | 25 |
| *Rhodotorula mucilaginosa* | 250 | 50 | 25 | 25 | 25 | 25 |
| *Trichoderma virens* | 750 | 62.5 | 62.5 | 37.5 | 25 | 25 |

* not determined

TABLE 21

| Strain | 9:1 | 4:1 | 3:2 | 1:4 |
|---|---|---|---|---|
| *Aspergillus brasiliensis* | 0.86 | 0.55 | 0.83 | * |
| *Candida albicans* | 0.38 | 0.56 | 0.46 | 0.82 |
| *Chaetomium globosum* | 0.36 | 0.48 | 0.86 | 0.81 |
| *Fusarium solani* | 0.38 | 0.56 | 0.46 | 0.82 |
| *Rhodotorula mucilaginosa* | 0.38 | 0.28 | 0.46 | 0.82 |
| *Trichoderma virens* | 0.33 | 0.57 | 0.63 | 0.81 |

* not determined

TABLE 22

|  | MIT | 9:1 | 4:1 | 3:2 | 2:3 | 1:4 | 1:9 | DGH |
|---|---|---|---|---|---|---|---|---|
| MIC [ppm] | 100 | 25 | 25 | 5 | 10 | 10 | 5 | 10 |
| SI |  | 0.48 | 0.70 | 0.23 | 0.64 | 0.82 | 0.46 |  |

TABLE 23

|  | MIT | 9:1 | 4:1 | DGH |
|---|---|---|---|---|
| MIC [ppm] | 250 | 50 | 25 | 10 |
| SI |  | 0.68 | 0.58 |  |

The above tables 18-23 clearly show that for two-component mixtures according to the invention of MIT and DGH in various mixing ratios, a marked synergism against various bacteria and fungi is present.

Example 5: Microbiological Load Test

A microbiological load test was used to test the susceptibility of water-based systems to microbial infestation and the effect of preservatives. For this, the preservatives were incorporated into the water-based systems in defined concentrations. To simulate conditions encountered in practice, the samples were subjected, following incorporation of the particular biocide products in the stated concentrations, to thermal treatment for 3 days at 60° C. in order to identify labile active ingredient constituents in the biocide products even in this phase of the experiment through subsequent ineffectiveness. Then, over an experiment period of 6 weeks, contamination with microorganisms was performed as stated below at weekly intervals such that after each contamination approx. $10^6$-$10^7$ bacteria per/g are present. 3 and 7 days after each contamination it was established by germ count determination whether complete killing (=0 bacteria per/g) or at least replication inhibition (to $10^5$-$10^1$ bacteria per/g) of the incorporated microorganisms has arisen compared to the non-preserved control samples.

As water-based system, a slurry of calcium carbonate (calcium carbonate slurry) with a solids fraction of 75% by weight was carried out. The microorganisms used for the experiment were the following types of bacteria in a mixture:

*Pseudomonas aeruginosa, Pseudomonas fluorescens, Pseudomonas oleovorans, Pseudomonas rubescens, Pseudomonas stutzeri, Alcaligenes faecalis, Citrobacter freuridii, Corynebacterium* sp.

A very good effectiveness is achieved if the preserved samples bring about complete killing (=0 bacteria per/g) of the incorporated microorganisms (3=very good). A good effect is present if a greatly reduced microbe level is observed (to $10^3$-$10^1$ bacteria per/g) compared to the non-preserved sample.

A moderate effect is present if, compared to the nonpreserved sample, a slightly reduced microbe level is observed (to $10^4$-$10^3$ bacteria per/g). A deficient effect is present if no or only a slight reduction in the microbe level is observed compared to the nonpreserved sample (to $10^7$-$10^5$ bacteria per/g).

The achieved results are given in table 24.

TABLE 24

| Dosage of the biocide mixtures | Week 1 | Week 2 | Week 3 | Week 4 | Week 5 | Week 6 |
|---|---|---|---|---|---|---|
| BIT/MIT (each 2.5%) | | | | | | |
| 500 ppm | 2 | 1 | 1 | 1 | 0 | 0 |
| 750 ppm | 3 | 2 | 1 | 1 | 0 | 0 |
| 1000 ppm | 3 | 3 | 2 | 1 | 0 | 0 |
| 500 ppm + 100 ppm DGH | 3 | 3 | 3 | 3 | 2 | 2 |

500 ppm: addition of 0.05% of a liquid mixture of BIT (2.5%) and MIT (2.5%) to the finished calcium carbonate slurry Assessment of the Preservation
0=deficient ($10^7$-$10^5$ bacteria per/g)
1=moderate ($10^4$-$10^3$ bacteria per/g)
2=good ($10^3$-$10^1$ bacteria per/g)
3=very good (0 bacteria per/g)

As the above table reveals, by adding DGH it is possible to boost the effect of mixtures of BIT and MIT known from the prior art, and antimicrobially, in particular antibacterially more resistant suspensions, dispersions or slurries of minerals, fillers or pigments result.

What is claimed is:

1. A biocidal substance comprising:
    (a) 1,2-benzisothiazolin-3-one and 2-methyl 4-isothiazolin-3-one; and
    (b) dodecylguanidine hydrochloride, wherein the 1,2-benzisothiazolin-3-one, the 2-methyl 4-isothiazolin-3-one, and the dodecylguanidine hydrochloride are present in a weight ratio effective for providing biocidal synergy.

2. The biocidal substance as claimed in claim 1, wherein:
    a weight ratio of components (a):(b) is 10:1 to 1:10; and
    a sum of components (a) and (b) is 1 to 80% by weight, based on the total weight of the biocidal substance.

3. The biocidal substance as claimed in claim 1, wherein a weight ratio of 1,2-benzisothiazolin-3-one to 2-methyl 4-isothiazolin-3-one is 1:100 to 100:1.

4. The biocidal substance as claimed in claim 1, wherein:
    a weight ratio of 1,2-benzisothiazolin-3-one to 2-methyl 4-isothiazolin-3-one is 1.5:1 to 1:2.5;
    a weight ratio of components (a):(b) is 2:1 to 1:5; and
    a sum of components (a) and (b) is 4 to 50% by weight, based on the total weight of the biocidal substance.

5. The biocidal substance as claimed in claim 1, further comprising, based on the total weight of the biocidal substance, 0.2 to 20% by weight of one or more further biocidal active ingredients selected from the group consisting of bronopol, benzylhemiformal, trimethylene-2-methylisothiazolinon-3-one, N-methylbenzisothiazolinone, 2-n-octylisothiazolin-3-one, tetramethylolacetylenediurea (TMAD), 1,3-bis(hydroxymethyl)-5,5-dimethylimidazolidine-2,4-dione (DMDMH), p-chloro-m-cresol, dimethylolurea, 1,2-dibromo-2,4-dicyanobutene, 2,2-dibromo-3-nitrilipropionamide, glutardialdehyde, ethylene glycol hemiformal, ethylene glycol bis-hemiformal, N-methylolurea, thiabendazole, carbendazim, zinc pyrithione, sodium pyrithione, 2-phenoxyethanol, phenoxypropanol, o-phenylphenol, chlorophene, quaternary ammonium salts, and 5-chloro-2-methyl-4-isothiazolin-3-one.

6. The biocidal substance as claimed in claim 1, wherein the biocidal substance contains no further biocidal active ingredients.

7. The biocidal substance as claimed in claim 1, wherein the biocidal substance is one of solutions, emulsions, suspensions, powders, foams, pastes, granules, aerosols and microencapsulations in polymeric substances.

8. The biocidal substance as claimed in claim 1, further comprising at least one of: interface-active substances, wetting agents, emulsifiers, dispersants, stabilizers, adhesives, thickeners, spreading agents, organic solvents, fragrances, dyes, buffer substances, buffer systems, pH regulators, solid carriers, and water.

9. A technical material containing the biocidal substance as claimed in claim 1.

10. The technical material as claimed in claim 9, wherein the technical material is selected from the group consisting of: a coating, a starch solution, a starch slurry, a product based on starch, a slurry of colored pigments, a slurry including both inorganic pigments and fillers, a construction chemical product, an adhesive based on animal raw materials, an adhesive based on vegetable raw materials, an adhesive based on synthetic raw materials, a polymer dispersion based on polyacrylate, a polymer dispersion based on polystyrene acrylate, a polymer dispersion based on styrene butadiene, a polymer dispersion based on polyvinyl acetate, a cleaner for industrial use, a cleaner for domestic use, a mineral oil, a mineral oil product, a cooling lubricant for metal working based on mineral oil-containing concentrates, a cooling lubricant for metal working based on semisynthetic concentrates, a cooling lubricant for metal working based on synthetic concentrates, an auxiliary for the leather industry, an auxiliary for the textile industry, an auxiliary for the photochemical industry, a pre-product of the chemical industry, an intermediate of the chemical industry, an ink, a wash, a wax emulsion, and a clay emulsion.

11. A method for protecting a technical material against infestation with microorganisms, for protecting a technical material from destruction by microorganisms, for controlling microorganisms on a technical material, or for controlling microorganisms in a technical material, the method comprising contacting the technical material with the biocidal substance of claim 1.

12. The biocidal substance as claimed in claim 1, wherein the biocidal substance does not include any of: interface-active substances, wetting agents, emulsifiers, dispersants, stabilizers, adhesives, thickeners, spreading agents, organic solvents, fragrances, dyes, buffer substances, buffer systems, pH regulators, solid carriers, and water.

* * * * *